(12) United States Patent
Silvestri

(10) Patent No.: US 7,112,727 B2
(45) Date of Patent: Sep. 26, 2006

(54) MUTANT ALLELE OF TOMATO

(75) Inventor: Giampaolo Silvestri, Torre dei Picendardi (IT)

(73) Assignee: Peotec Seeds S.r.l., Parma (IT)

( * ) Notice: Subject to any disclaimer, the term of this patent is extended or adjusted under 35 U.S.C. 154(b) by 501 days.

(21) Appl. No.: 10/327,625

(22) Filed: Dec. 20, 2002

(65) Prior Publication Data

US 2004/0123351 A1 Jun. 24, 2004

(51) Int. Cl.
*A01H 5/00* (2006.01)
*A01H 5/10* (2006.01)
*A01H 1/00* (2006.01)
*A01H 1/02* (2006.01)
*C12N 5/04* (2006.01)

(52) U.S. Cl. .................. 800/317.4; 800/260; 800/263; 800/266; 800/268; 435/411; 435/423; 435/430; 435/430.1

(58) Field of Classification Search ............... 800/260, 800/263, 266, 268, 317.4, 269; 435/411, 435/423, 430, 430.1, 421
See application file for complete search history.

(56) References Cited

U.S. PATENT DOCUMENTS 4,734,369 A * 3/1988 Evans et al. ................ 800/270
5,434,344 A * 7/1995 Bennett et al. ............. 800/263
5,523,520 A * 6/1996 Hunsperger et al. ........ 800/260

OTHER PUBLICATIONS

Kraft et al. Theor. Appl. Genet. 101: 323–326 (2000).*
Eshed et al. Genetics 143: 1807–1817 (1996).*
Osborn et al. Theor. Appl. Genet. 73: 350–356 (1987).*
Chetelat et al. Plant Journal 4(4): 643–650 (1993).*
Azanza et al. Theor. Appl. Genet. 87: 965–972 (1994).*
Eshed, et al., 1996, Less–Than–Additive Epistatic Interactions of Quantitative Trait Loci in Tomato, Genetics, vol. 143, pp. 1807–1817.
Kraft, et al., 2000, Linkage Disequilibrium and Fingerprinting in Sugar Beet, Theoretical Applied Genetics, vol. 101, pp. 323–326.

* cited by examiner

*Primary Examiner*—David T. Fox
*Assistant Examiner*—Keith O. Robinson
(74) *Attorney, Agent, or Firm*—Jondle & Associates, P.C.

(57) ABSTRACT

This invention relates to a tomato plant, seed, variety and hybrid. More specifically, the invention relates to a tomato plant having a mutant allele for allflesh which results in the tomato fruit having a cavity area which is solid and lacks a gel or liquid. The invention also relates to crossing inbreds, varieties and hybrids containing the allflesh allele to produce novel types and varieties of tomato plants.

13 Claims, 3 Drawing Sheets

MUTANT ALLELE OF TOMATO

FIELD OF INVENTION

The present invention relates to a novel allflesh allele of tomato designated "PSAF", which results in the tomato fruit having a cavity area which is solid and lacks a gel or liquid content. This present invention also relates to a tomato seed, a tomato plant, a tomato variety and a tomato hybrid, which contain the allflesh allele. In addition, the present invention is directed to transferring the allflesh allele in the tomato plant to other tomato varieties and species and is useful for producing novel types and varieties of allflesh tomato.

BACKGROUND OF THE INVENTION

The present invention relates to a new and distinctive tomato mutant allele, designated "PSAF" for Peotec Seeds allflesh. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as firmness, color, content in soluble solids, acidity and viscosity, resistance to diseases and insects, and tolerance to drought and heat. With mechanical harvesting of the tomato fruits for process purpose, i.e. juice, paste, catsup, etc, uniformity of plant characteristics such as germination, growth rate, maturity and plant uniformity is also important.

Practically speaking, all cultivated and commercial forms of tomato belong to a species most frequently referred to as *Lycopersicon esculentum* Miller. Lycopersicon is a relatively small genus within the extremely large and diverse family *Solanaceae* which is considered to consist of around 90 genera, including pepper, tobacco and eggplant. The genus *Lycopersicon* has been divided into two subgenera, the *esculentum* complex which contains those species that can easily be crossed with the commercial tomato and the peruvianum complex which contains those species which are crossed with considerable difficulty (Stevens, M., and Rick, C. M. 1986. Genetics and Breeding. In: The Tomato Crop. A scientific basis for improvement, pp. 35–109. Atherton, J., Rudich, G. (eds.). Chapman and Hall, New York). Due to its value as a crop, *L. esculentum* Miller has become widely disseminated all over the world. Even if the precise origin of the cultivated tomato is still somewhat unclear, it seems to come form the Americas, being native to Ecuador, Peru and the Galapagos Island and initially cultivated by Aztecs and Incas as early as 700 AD. Mexico appears to have been the site of domestication and the source of the earliest introduction. It is supposed that the cherry tomato, *L. esculentum* var. *cerasiforme*, is the direct ancestor of modem cultivated forms.

Tomato is grown for its fruit, widely used as a fresh market or processed product. As a crop, tomato is grown commercially wherever environmental conditions permit the production of an economically viable yield. In California, the first largest process market and second largest fresh market in the United States, processing tomato are harvested by machine. The majority of fresh market tomatoes are harvested by hand at vine ripe and mature green stage of ripeness. Fresh market tomatoes are available in the United States year round. Process tomato season in California is from late June to September. Process tomato are used in many forms, as canned tomatoes, tomato juice, tomato sauce, puree, paste or even catsup. Over the 500,000 acres of tomatoes that are grown annually in the US, approximately 40% are grown for fresh market consumption, the balance are grown for processing.

Tomato is a simple diploid species with twelve pairs of differentiated chromosomes. The cultivated tomato is self fertile and almost exclusively self-pollinating. The tomato flowers are hermaphrodites. Commercial cultivars were initially open pollinated. Most have now been replaced by better yielding hybrids. Due to its wide dissemination and high value, tomato has been intensively bred. This explains why such a wide array of tomato are now available. The shape may range from small to large, and there are cherry, plum, pear, standard, and beefsteak types. Tomatoes may be grouped by the amount of time it takes for the plants to mature fruit for harvest and, in general the cultivars are considered to be early, midseason or late-maturing.

Tomatoes can also be grouped by the plant's growth habit; determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants will tend to have tomato fruit in different stages of maturity at any given time. More recent developments in tomato breeding have led to a wider array of fruit color. In addition to the standard red ripe color, tomatoes can be creamy white, lime green, pink, yellow, golden, or orange.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior tomato inbreds and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same tomato traits.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new tomato varieties.

The development of commercial tomato hybrids requires the development of homozygous inbred lines, the crossing of these lines, and the evaluation of the crosses. Pedigree, backcross or recurrent selection breeding methods are used to develop lines from breeding populations. Breeding programs combine desirable traits from two or more lines or various broad-based sources into breeding pools from which mutant alleles are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred parents of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars or new parents for hybrids.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbreds are crossed to produce the $F_1$ progeny.

Tomato is an important and valuable field crop. Thus, a continuing goal of plant breeders is to develop stable, high yielding tomato hybrids that are agronomically sound. The reasons for this goal are obviously to maximize the amount of fruit produced on the land used as well as to improve the fruit qualities. To accomplish this goal, the tomato breeder must select and develop tomato plants that have the traits that result in superior parental lines for producing hybrids.

SUMMARY OF THE INVENTION

Figure 1:
FIG. 1 shows tomato fruits having the allflesh trait of the present invention and showing one fruit cut in half.
Figure 2:
FIG. 2 shows tomato fruits having the allflesh trait of the present invention and showing one fruit diced.
Figure 3:
FIG. 3 shows normal tomato fruits with one fruit cut in half.

According to the invention, there is provided a novel mutant allele, designated "PSAF". This invention thus relates to a tomato seed, a tomato plant, a tomato variety, a tomato hybrid and to a method of producing a tomato plant. More specifically, the invention relates to a mutant allele designated PSAF which when present as a homozygous recessive produces a tomato fruit having solid cavity areas and lacking the gel or liquid which is present in the cavities of normal tomato fruits.

Another aspect of the invention relates to any tomato seed or plant having the mutant allele PSAF.

In another aspect, the present invention provides regenerable cells for use in tissue culture. The tissue culture will preferably be capable of regenerating plants having the physiological and morphological characteristics of the foregoing inbred tomato plant, and of regenerating plants having substantially the same genotype as the foregoing inbred tomato plant. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides tomato plants regenerated from the tissue cultures of the invention.

Another objective of the invention is to provide methods for producing other inbred tomato plants derived from a tomato plant having the PSAF allele. Tomato lines derived by the use of those methods are also part of the invention.

The invention also relates to methods for producing a tomato plant containing in its genetic material one or more transgenes and to the transgenic tomato plant produced by that method.

The invention further provides methods for developing tomato plant in a tomato plant breeding program using plant breeding technique including recurrent selection, backcrossing, pedigree breeding, restriction fragment length polymorphism enhanced selection, genetic marker enhanced selection and transformation. Seeds, tomato plant, and parties thereof produced by such breeding methods are also part of the invention.

DETAILED DESCRIPTION OF THE INVENTION

DEFINITIONS

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids. Soluble solids refers to the percent of solid material found in the fruit tissue, the vast majority of which is sugars. Soluble solids are directly related to finished processed product yield of pastes and sauces. Soluble solids are estimated with a refractometer, and measured as degrees brix.

pH: the pH is a measure of acidity in fresh tomato juice. A pH under 4.35 is desirable to prevent bacterial spoilage of finished products. pH rises as fruit matures.

Viscosity: the viscosity or consistency of tomato products is affected by the degree of concentration of the tomato, the amount of and extent of degradation of pectine, the size, shape and quality of the pulp, and probably to a lesser extent, by the proteins, sugars and other soluble constituents. The viscosity is measured in Bostwick centimeters by using instruments such as a Bostwick Consistometer.

Quantitative Trait Loci (QTL) Quantitative trait loci refer to genetic loci that control to some degree numerically representable traits that are usually continuously distributed.

Predicted paste bostwick: the predicted paste bostwick is the flow distance of tomato paste diluted to 12 degrees brix and heated prior to evaluation. Dilution to 12 degrees brix for bostwick measurement is a standard method used by industry to evaluate product consistency. The lower the number, the thicker the product and therefore more desirable in consistency oriented products such as catsup. The following formula is usually used to evaluate the predicted paste bostwick: Predicted paste bostwick=−11.53+ (1.64*juice brix)+(0.5*juice bostwick)

Determinate tomatoes: varieties that come to fruit all at once, then stop bearing. They are best suited for commercial growing since they can be harvested all at once.

Relative maturity: relative maturity is an indication of time until a tomato genotype is ready for harvest. A genotype is ready for harvest when 90% or more of the tomatoes are ripe.

Semi-erect habit: a semi-erect plant has a combination of lateral and upright branching and has an intermediate type habit between a prostate plant habit, having laterally growing branching with fruits most of the time on the ground and an erect plant habit with branching going straight up with fruit being off the ground.

Medium size fruits: a tomato plant bearing medium size fruits has fruit weights ranging from 70 to 85 grams.

Deep globe shade: a tomato fruit being slightly wider than longer but still having a round shape.

Flesh color: the color of the tomato flesh that can range from orange-red to dark red when at ripe stage (harvest maturity).

Uniform ripening: a tomato that ripens uniformly, i.e., that has no green discoloration on the shoulders. The uniform ripening is controlled by a single recessive gene.

Allflesh (AF): As used herein, the allflesh characteristic results from the mutant recessive allele PSAF of the present invention. Allflesh means a tomato fruit which does not have a gel or liquid surrounding the tomato seeds in the fruit cavity area. Allflesh tomatoes have fruit cavity areas which are solid and can be more easily processed compared to normal tomatoes which contain a gel or liquid substance in the fruit cavities.

Normal Flesh: As used herein, normal flesh means a tomato fruit that does not express the allflesh characteristic.

Potential Yield: As used herein, "potential yield" is expressed in tons/ha or tons/acre and is the sum of marketable fruits, green (unripe) fruits and rotten fruits. Potential yield also may be referred to as total yield.

Juice Bostwich: Juice viscosity indication measured by Bostwich device, expressed in cm of juice per 30 seconds.

Wall thickness: Fruit wall thickness measured in millimeters (mm).

Percent (%) Brix/ton: As used herein, the % brixiton is the weight of soluble solids in a ton of fruits.

Percent (%) Broken: The percent of fruit with broken skin due to mechanical harvest.

Percent (%) Stems: Percent of stems attached to the fruit after harvest.

The present invention relates to a novel allele designated "PSAF" in the genus Lycopersicon that is phenotypically expressed in a more solid fruit cavity with a reduced gel or liquid present. As the term is used herein, allflesh refers to a condition where the seed cavity of the fruits is solid and processable instead of being liquids as in other tomatoes. Squeezing an allflesh tomato results in a lack of gel or liquid drainage from the fruit.

According to the invention, there is provided a novel mutant allele, designated "PSAF". This invention thus relates to a tomato seed, a tomato plant, a tomato variety, a tomato hybrid and to a method of producing a tomato plant. More specifically, the invention relates to a mutant allele designated PSAF which when present as a homozygous recessive produces a tomato fruit having solid cavity areas and lacking the gel or liquid which is present in the cavities of normal tomato fruits.

Another aspect of this invention relates to any tomato seed or plant having the mutant allele PSAF.

In one aspect of the invention, the tomato of the present invention when processed results in a product having a higher solids content than other commercial tomatoes presently grown. In another aspect the PSAF tomato of the present invention results in little or no loss of weight after harvest and during the transport of the tomato fruits from the field to the processing factory. In normal tomatoes, approximately 5% of weight is lost due to the liquid that drains away during field operations and transportation. Also, road pollution is dramatically reduced during transportation since tomatoes of the present invention do not release liquid normally dispersed by trucks. Allflesh tomatoes have an improved resistance to over-ripening.

Allflesh tomatoes of the present invention have additional advantages for the processor. In the processing of diced tomatoes the allflesh fruit is 100% processable which results in approximately 50% more diced tomatoes from the same amount of raw product when compared to normal tomatoes. This is a substantial financial advantage. For wholepeel tomatoes, even after months in the can the allflesh fruits do not collapse and keep their original shape and firmness better than normal tomatoes. Also, allflesh tomatoes have a better color and a higher sugar content and better flavor than normal tomatoes.

The genetic factor of the present invention which is capable of transmitting the allflesh characteristic has been determined to be a mutant single recessive allele, which has been designated "PSAF". It is a feature of the present invention that this single mutant allele PSAF may be used in and transferred to different tomato varieties and to other tomato species.

The tomato plant of the invention may further comprise, or have, a cytoplasmic factor or other factor that is capable of conferring male sterility. Male sterility may also be provided by nuclear genes such as the recessive ms gene. Parts of the tomato plant of the present invention are also provided, such as e.g., pollen obtained from an inbred plant and an ovule of the inbred plant.

In another aspect, the present invention provides regenerable cells for use in tissue culture. The tissue culture will preferably be capable of regenerating plants having the physiological and morphological characteristics of the foregoing inbred tomato plant, and of regenerating plants having substantially the same genotype as the foregoing inbred tomato plant. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides tomato plants regenerated from the tissue cultures of the invention.

Another objective of the invention is to provide methods for producing other inbred tomato plants derived from a tomato plant having the PSAF allele. Tomato lines derived by the use of those methods are also part of the invention.

The invention also relates to methods for producing a tomato plant containing in its genetic material one or more transgenes and to the transgenic tomato plant produced by that method.

In another aspect, the present invention provides for single gene converted plants of PSAF. The single transferred gene may preferably be a dominant or recessive allele. Preferably, the single transferred gene will confer such trait as male sterility, herbicide resistance, Insect resistance, resistance for bacterial, fungal, or viral disease, male fertility, improved harvest characteristics, enhanced nutritional quality, improved processing characteristics. The single gene may be a naturally occurring tomato gene or a transgene introduced through genetic engineering techniques.

The invention further provides methods for developing tomato plant in a tomato plant breeding program using plant breeding technique including recurrent selection, backcrossing, pedigree breeding, restriction fragment length polymorphism enhanced selection, genetic marker enhanced selection and transformation. Seeds, tomato plant, and parties thereof produced by such breeding methods are also part of the invention.

This present invention is directed to developing unique plants of the Lycopersicon species. The tomato fruit of the present invention expresses a substantial increase in soluble solids. A transferable gene or allele that conveys this characteristic has been isolated and incorporated into other genetic backgrounds. The allele of the instant invention has also been expressed in different genetic backgrounds of tomato. To date, except for the present invention, there is no known allflesh characteristic in any cultivars of tomato.

As used herein, the term plant includes plant cells, plant protoplasts, plant cell tissue cultures from which cleome plants can be regenerated, plant calli, plant clumps and plant cells that are intact in plants or parts of plants, such as embryos, pollen, ovules, flowers, stems, leaves, roots, root tips, anthers and the like.

EXAMPLES

The following examples are provided to further illustrate the present invention and are not intended to limit the invention beyond the limitations set forth in the appended claims.

Example 1

This previously unknown allflesh characteristic arose from a research field in 1982 from an $F_3$ plant designated PS17 having the pedigree [[[(Louis×Roma VF)×(CS161/69×Laurano) $F_3$]×[L. pimpinellifolium×(Titano×P301S) $BC_3S_3$]]×(Chico×L.64×Vis×P310) $F_3$]]]–17.

The allflesh phenotype of the present invention generally segregates as a simple recessive allele, yielding an $F_2$ segregation of 1 allflesh to 1 normal from an (allflesh× normal) cross, and 1 allflesh to 1 normal from an (allflesh× normal)×allflesh backcross. The degree of allflesh may vary slightly between different backgrounds as shown in Tables 1–18.

Example 2

Development of Allflesh 1000 $F_1$. Hybrid Seeds and Plants

As shown in Table 1, Allflesh (AF) $F_5$ tomato line LA3291 was crossed to Allflesh LA3292 in 1998 to produce the Allflesh $F_1$ hybrid. In 1999 and 2000, AF PLV5342 was crossed with PLV5330 to produce Allflesh $F_1$ hybrid seed. AF1000 is a determinate, round-oval shaped, for processing (paste, diced).

TABLE 1

| PEDIGREE | GENERATION | YEAR |
|---|---|---|
| Female | | |
| LA 3291 (AF) | F5 | 1998 |
| PLV 5342 (AF) | F6 | 1999 |
| PLV 5342 (AF) | F7 | 2000 |
| Male | | |
| LA 3292 (AF) | F5 | 1998 |
| PLV 5330 (AF) | F6 | 1999 |
| PLV 5330 (AF) | F7 | 2000 |
| Pedigree Hybrid | | |
| LA 3291 F5 × LA 3292 F5 | F1 | 1999 |
| PLV 5342 × PLV 5330 | F1 | 2000 |
| PLV 5342 × PLV 5330 (AF1000) | F1 | 2001 |
| PLV 5342 × PLV 5330 (AF1000) | F1 | 2002 |

Example 3

Development of Allflesh 900 $F_1$ Hybrid Seeds and Plants

As shown in Table 2, Allflesh tomato line PLV 5337 was crossed to Allflesh tomato line PLV5329 to produce AF900 which is a determinate, elongated fruit, Italian peeling type tomato.

TABLE 2

| PEDIGREE | GENERATION | YEAR | REMARKS |
|---|---|---|---|
| Female | | | |
| LA 3286 (AF) | F5 | 1998 | Selection |
| PLV 5337 (AF) | F6 | 1999 | Selection |
| PLV 5337 (AF) | F7 | 2000 | Selection |
| Male | | | |
| LA 3287 (AF) | F5 | 1998 | Selection |
| PLV 5329 (AF) | F6 | 1999 | Selection |
| PLV 5329 (AF) | F7 | 2000 | Selection |
| Pedigree Hybrid | | | |
| LA 3286 F5 × LA 3287 F5 | F1 | 1999 | Screening trial |
| PLV 5337 × PLV 5329 | F1 | 2000 | 1st Level Trial |
| PLV 5337 × PLV 5329 | F1 | 2001 | 2nd Level Trial |
| PLV 5337 × PLV 5329 (AF900) | F1 | 2002 | Pre-commercial |

Example 4

Development of Tomato AF1038 $F_1$ Hybrid Seeds and Plants

As shown in Table 3, Allflesh tomato line PLV 5337 was crossed to Allflesh tomato line PLV5329 to produce AF1038 $F_1$ which is a determinate, square-round fruit for processing (paste, diced, whole peel).

TABLE 3

| PEDIGREE | GENERATION | YEAR |
|---|---|---|
| Female | | |
| LA 3291 (AF) × PO362X42 F4 | F1 | 1998 |
| SSD 1A | F2 | 1999 |
| SSD 1A | F3 | 1999 |
| SSD 1A | F4 | 2000 |
| SSD 1A | F5 | 2000 |
| PLV 5336 (AF) | F6 | 2001 |
| Male | | |
| LA 3293 F5 (AF) × PO39OX612 F5 | F1 | 1998 |
| SSD 2A | F2 | 1999 |
| SSD 2A | F3 | 1999 |
| SSD 2A | F4 | 2000 |
| SSD 2A | F5 | 2000 |
| PLV 5333 | F6 | 2001 |
| Pedigree Hybrid | | |
| PLV 5336 F6 × PLV 5333 F6 | F1 | 2001 |
| PLV 5336 F6 × PLV 5333 F6 | F1 | 2001 |
| PLV 5336 F6 × PLV 5333 F6 (1038) | F1 | 2002 |

Example 5

Development of Tomato AF 1039 $F_1$ Hybrid Seeds and Plants

As shown in Table 4, Allflesh tomato line PLV 5340 was crossed to Allflesh tomato line PLV 5341 to produce AF 1039 which is a determinate, elongated fruit, Italian peeling type suitable for mechanical harvest.

TABLE 4

| PEDIGREE | GENERATION | YEAR |
|---|---|---|
| Female | | |
| LA 3286 (AF) × PO390X41 F4 | F1 | 1998 |
| SSD 4A | F2 | 1999 |
| SSD 4A | F3 | 1999 |
| SSD 4A | F4 | 2000 |
| SSD 4A | F5 | 2000 |
| PLV 5340 (AF) | F6 | 2001 |

TABLE 4-continued

| PEDIGREE | GENERATION | YEAR |
|---|---|---|
| Male | | |
| LA 3287 F5 (AF) × P0388X6BC1S2 | F1 | 1998 |
| SSD 3A | F2 | 1999 |
| SSD 3A | F3 | 1999 |
| SSD 3A | F4 | 2000 |
| SSD 3A | F5 | 2000 |
| PLV 5341 (AF) | F6 | 2001 |
| Pedigree Hybrid | | |
| PLV 5340 F6 × PLV 5341 F6 (1039) | F1 | 2001 |

Example 6

Development of Tomato AF PLX 1502 $F_1$ Hybrid Seeds and Plants

As shown in Table 5, Allflesh tomato line PLV 5422 was crossed to Allflesh tomato line PLV 5423 to produce AF PLX 1502 which is a determinate, oval, saladette type for fresh market and processing suitable for hand picking.

TABLE 5

| PEDIGREE | GENERATION | YEAR |
|---|---|---|
| Female | | |
| LA 3286 F5 (AF) × P0390X52 F4 | F1 | 1998 |
| SSD 5A | F2 | 1999 |
| SSD 5A | F3 | 1999 |
| SSD 5A | F4 | 2000 |
| SSD 5A | F5 | 2000 |
| PLV 5422 (AF) | F6 | 2001 |
| Male | | |
| LA 3302 F3 (AF) × PO212X4 BC1S2 | F1 | 1998 |
| SSD 6A | F2 | 1999 |
| SSD 6A | F3 | 1999 |
| SSD 6A | F4 | 2000 |
| SSD 6A | F5 | 2000 |
| PLV 5423 | F6 | 2001 |
| Pedigree Hybrid | | |
| PLV 5422 F6 × PLV 5423 F6 (PLX 1502 AF) | F1 | 2001 |

Example 7

Development of Tomato AF PLX 2539 $F_1$ Hybrid Seeds and Plants

As shown in Table 6, Allflesh tomato line PLV 5426 was crossed to Allflesh tomato line PLV 5428 to produce AF PLX 2539 which is a determinate, round shaped, determinate cherry, for processing and fresh market.

TABLE 6

| PEDIGREE | GENERATION | YEAR |
|---|---|---|
| Female | | |
| LA 3291 F5 (AF) × PO532X4 F3 | F1 | 1998 |
| SSD 7C | F2 | 1999 |
| SSD 7C | F3 | 1999 |
| SSD 7C | F4 | 2000 |
| SSD 7C | F5 | 2000 |
| PLV 5426 (AF) | F6 | 2001 |

TABLE 6-continued

| PEDIGREE | GENERATION | YEAR |
|---|---|---|
| Male | | |
| LA 3287 F3 (AF) × PO533X2 BC1S2 | F1 | 1998 |
| SSD 9C | F2 | 1999 |
| SSD 9C | F3 | 1999 |
| SSD 9C | F4 | 2000 |
| SSD 9C | F5 | 2000 |
| PLV 5428 | F6 | 2001 |
| Pedigree Hybrid | | |
| PLV 5426 F6 × PLV 5428 F6 (PLX 2539 AF) | F1 | 2002 |

Example 8

Development of Tomato AF PLX 1272 $F_1$ Hybrid Seeds and Plants

As shown in Table 7, Allflesh tomato line PLV 0334 was crossed to Allflesh tomato line PLV 0336 to produce AF 1272 which is a determinate, round shaped, big fruited, multilocular for fresh market.

TABLE 7

| PEDIGREE | GENERATION | YEAR |
|---|---|---|
| Female | | |
| LA 3339 F3 (AF) × M0633X312 F5 | F1 | 1998 |
| SSD 9D | F2 | 1999 |
| SSD 9D | F3 | 1999 |
| SSD 9D | F4 | 2000 |
| SSD 9D | F5 | 2000 |
| PLV 0334 (AF) | F6 | 2001 |
| Male | | |
| LA 3341 F3 (AF) × M0638X62 F4 | F1 | 1998 |
| SSD 11D | F2 | 1999 |
| SSD 11D | F3 | 1999 |
| SSD 11D | F4 | 2000 |
| SSD 11D | F5 | 2000 |
| PLV 0336 (AF) | F6 | 2001 |
| Pedigree Hybrid | | |
| PLV 0334 F6 × PLV 0336 F6 (1272 AF) | F1 | 2002 |

Example 9

Development of Tomato AF PLX 2070 $F_1$ Hybrid Seeds and Plants

As shown in Table 8, Allflesh tomato line PLV 0337 was crossed to Allflesh tomato line PLV 0340 to produce AF PLX 2070 which is a indeterminate, round shaped, cherry, for fresh market, for greenhouse and open field.

TABLE 8

| PEDIGREE | GENERATION | YEAR |
|---|---|---|
| Female | | |
| LA 3291 F5 (AF) × M0655X5 BC1S2 | F1 | 1998 |
| SSD 14C | F2 | 1999 |
| SSD 14C | F3 | 1999 |
| SSD 14C | F4 | 2000 |
| SSD 14C | F5 | 2000 |
| PLV 0337 (AF) | F6 | 2001 |

TABLE 8-continued

| PEDIGREE | GENERATION | YEAR |
|---|---|---|
| Male | | |
| LA 3287 F5 (AF) × M0656X4 BC1S2 | F1 | 1998 |
| SSD 15C | F2 | 1999 |
| SSD 15C | F3 | 1999 |
| SSD 15C | F4 | 2000 |
| SSD 15C | F5 | 2000 |
| PLV 0340 (AF) | F6 | 2001 |
| Pedigree Hybrid | | |
| PLV 0337 F6 × PLV 0340 F6 (PLX 2070 AF) | F1 | 2002 |

Example 10

Development of Tomato AF PLX 2168 $F_1$. Hybrid Seeds and Plants

As shown in Table 9, Allflesh tomato line PLV 0338 was crossed to Allflesh tomato line PLV 0339 to produce AF PLX 2168 which is an indeterminate, round shaped for fresh market and greenhouse.

TABLE 9

| PEDIGREE | GENERATION | YEAR |
|---|---|---|
| Female | | |
| LA 3340 F3 (AF) × M0274X435 F5 | F1 | 1998 |
| SSD 16M | F2 | 1999 |
| SSD 16M | F3 | 1999 |
| SSD 16M | F4 | 2000 |
| SSD 16M | F5 | 2000 |
| PLV 0338 (AF) | F6 | 2001 |
| Male | | |
| LA 3341 F3 (AF) × M0450X72 F4 | F1 | 1998 |
| SSD 18M | F2 | 1999 |
| SSD 18M | F3 | 1999 |
| SSD 18M | F4 | 2000 |
| SSD 18M | F5 | 2000 |
| PLV 0339 (AF) | F6 | 2001 |
| Pedigree Hybrid | | |
| PLV 0338 F6 × PLV 0339 F6 (PLX 2168 AF) | F1 | 2002 |

Example 11

Development of Tomato AF PLX 9007$F_1$ Hybrid Seeds and Plants

As shown in Table 10, Allflesh tomato line PLV 0335 F6 was crossed to Allflesh tomato line PLV 0341 F6 to produce AF PLX 9007 which is an indeterminate, oval shaped, bilocular for fresh market and open field.

TABLE 10

| PEDIGREE | GENERATION | YEAR |
|---|---|---|
| Female | | |
| LA 3340 F3 (AF) × MO274X14 F4 | F1 | 1998 |
| SSD 19M | F2 | 1999 |
| SSD 19M | F3 | 1999 |
| SSD 19M | F4 | 2000 |
| SSD 19M | F5 | 2000 |

TABLE 10-continued

| PEDIGREE | GENERATION | YEAR |
|---|---|---|
| PLV 0335 (AF) | F6 | 2001 |
| Male | | |
| LA 3341 F3 (AF) × P0388X54 BC1S3 | F1 | 1998 |
| SSD 20M | F2 | 1999 |
| SSD 20M | F3 | 1999 |
| SSD 20M | F4 | 2000 |
| SSD 20M | F5 | 2000 |
| PLV 0341 (AF) | F6 | 2001 |
| Pedigree Hybrid | | |
| PLV 0335 F6 × PLV 0341 F6 (PLX 9007 AF) | F1 | 2002 |

Example 12

Allflesh Mutant Allele

As shown in Table 11, the mutant Allflesh allele is a single recessive allele. Crosses between normal line × Allflesh had the following results:

TABLE 11

| Cross | Pedigree | Year | F1 Hybrid Results |
|---|---|---|---|
| A) Female Normal flesh | Ace | 1983 | F1 = 100% Normal flesh |
| Male Allflesh | LS 1 | 1983 | |
| B) Female Allflesh | LS 1 | 1983 | F1 = 100% Normal flesh |
| Male Normal flesh | Ace | 1983 | |
| A) Female Normal flesh | UC82 | 1998 | F1 = 100% Normal flesh |
| Male Allflesh | LA 3291 | 1998 | |
| B) Female Allflesh | LA 3291 | 1998 | F1 = 100% Normal flesh |
| Male Normal flesh | UC 82 | 1998 | |
| C) Female Allflesh | LA 3291 | 1998 | F1 = 100% Allflesh |
| Male Allflesh | LA 3292 | 1998 | (Allflesh 1000) |
| A) Female Normal flesh | Roma VF | 1998 | F1 = 100% Normal flesh |
| Male Allflesh | LA 3286 | 1998 | |
| B) Female Allflesh | LA 3286 | 1998 | F1 = 100% Normal flesh |
| Male Normal flesh | Roma VF | 1998 | |
| C) Female Allflesh | LA 3286 | 1998 | F1 = 100% Allflesh |
| Male Allflesh | LA 3287 | 1998 | (Allflesh 900) |

Example 13

Evaluation f $F_2$ Progeni s

As shown below, the $F_2$ populations segregated in a ratio of 1AF to 3 Normal. In order to obtain an Allflesh $F_1$ hybrid, both parents must have the Allflesh recessive allele.

| | | | |
|---|---|---|---|
| A) | Female Normal flesh × Male Allflesh F2 progeny | | |
| | Pedigree: (Ace × LS 1AF) F2 | | |
| | Results: Plants with Allflesh character | | 241 |
| | Plants with Normal flesh character | | 769 |
| B) | Female Allflesh × Male Normal flesh F2 progeny | | |
| | Pedigree: (LS1AF × Ace) F2 | | |
| | Results: Plants with Allflesh character | | 261 |
| | Plants with Normal flesh character | | 739 |
| C) | Female Normal flesh × Male Allflesh F2 progeny | | |
| | Pedigree: (UC82 × LA 3291AF) F2 | | |
| | Results: Plants with Allflesh character | | 265 |
| | Plants with Normal flesh character | | 735 |
| D) | Female Allflesh × Male Normal flesh F2 progeny | | |
| | Pedigree: (LA 3291AF × UC 82) F2 | | |
| | Results: Plants with Allflesh character | | 240 |
| | Plants with Normal flesh character | | 760 |
| E) | Female Allflesh × Male Allflesh F2 progeny | | |

-continued

|   | Pedigree: | (LA 3291AF × LA 3192AF) F2 | |
|---|---|---|---|
|   | Results: | Plants with Allflesh character | 1000 |
|   |   | Plants with Normal flesh character | 0 |
| F) | Female Normal flesh × Male Allflesh F2 progeny | | |
|   | Pedigree: | (Roma VF × LA 3286AF) F2 | |
|   | Results: | Plants with Allflesh character | 238 |
|   |   | Plants with Normal flesh character | 762 |
| G) | Female Allflesh × Male Normal flesh F2 progeny | | |
|   | Pedigree: | (LA 3286AF × Roma VF) F2 | |
|   | Results: | Plants with Allflesh character | 244 |
|   |   | Plants with Normal flesh character | 756 |
| H) | Female Allflesh × Male Allflesh F2 progeny | | |
|   | Pedigree: | (LA 3286AF × LA 3287AF) F2 | |
|   | Results: | Plants with Allflesh character | 1000 |
|   |   | Plants with Normal flesh character | 0 |

Example 14

Average Production Value

Table 12 shows production data for four allflesh hybrids suitable for paste and diced production (TO 1038, AF 1120, AF 1000 and TO 930) versus commercial Perfectpeel, the most used hybrid for these purposes. Three out of four of these allflesh outperformed Perfectpeel. The low percentage of bad and rotten tomatoes is a sign of healthy fruit, especially for Allflesh 1120 which is considered the earlier variety. The allflesh hybrids had the advantages of: 1) dependable and constant yield because of the improved resistance to over ripening and long shelf life; 2) superior flesh content; 3) higher viscosity; and 4) color and brix help to reduce processing cost and time.

TABLE 12

| Hybrid | Commercial t/ha | Unripe % | Rotten % | Avg weight g/fruit | yield t/ha |
|---|---|---|---|---|---|
| TO 1038 | 78 | 91.8 | 5.8 | 2.4 | 72 | 85 |
| Allflesh 1120 | 67.8 | 93 | 4.7 | 2.6 | 87 | 72.9 |
| Allflesh 1000 | 78.4 | 91.1 | 7.6 | 1.3 | 84 | 86.1 |
| TO 930 | 79 | 89.9 | 8.7 | 1.4 | 74 | 87.9 |
| Perfectpeel | 74.8 | 88.8 | 7.9 | 3.3 | 76 | 84.2 |

Example 15

Peeling Tomatoes with 8% Bx Juic

Analysis of Raw Product

TABLE 13

| Trait | TO 0900 (Allflesh) | Hypeel 244 (Normal) |
|---|---|---|
| R.O. (EBrix) | 6.33 | 5.85 |
| PH | 4.41 | 4.42 |
| Color | | |
| L | 24.39 | 23.86 |
| a | 29.03 | 28.14 |
| b | 13.78 | 13.64 |
| a/b | 2.14 | 2.06 |
| Acidity (g/100 g) | 0.45 | 0.45 |
| Fruit firmness | Excellent | Normal |
| Sugar (g/100 g) | 3.87 | 3.38 |
| % ZZ/R.R. Ratio | 61.05 | 57.74 |
| Net weight cans | 849.63 | 841.73 |
| Weight of dripped product | 691.53 | 709.53 |
| % Dripped | 81.4 | 84.3 |
| Weight of whole fruits | 691.53 | 664.73 |
| Wholeness % | 100 | 93.77 |
| Skin cm2/can | 8.67 | 12.67 |
| Skin (cm2/100 g) | 1.02 | 1.51 |
| Necrosys | 1/3 scatole | 1/3 scatole |

TABLE 14

| Variety | Company | Avg Wt | % Stems | % Broken | Wall (mm) | Raw Brix | pH | J Bost | PP Bost | Serum V |
|---|---|---|---|---|---|---|---|---|---|---|
| TO 1036 | Peotec | 54.63 | 0.87 | 0 | 5.96 | 5.29 | 4.4 | 14.12 | 3.79 | 491.82 |
| AF 905 | Peotec | 70.7 | 2.45 | 0 | 6.17 | 6.41 | 4.5 | 12.2 | 4.58 | 392.52 |
| AF 1000 | Peotec | 57.79 | 1.61 | 0.55 | 6.1 | 5.94 | 4.5 | 13.35 | 4.42 | 419.79 |
| AF 900 | Peotec | 85.93 | 2.56 | 0 | 6.03 | 5.18 | 4.6 | 14.08 | 3.6 | 227.47 |
| AB2 | DeRuiter | 101.3 | 0.76 | 0 | 7.21 | 5.26 | 4.4 | 17.82 | 5.6 | 358.5 |
| APT539 | Asgrow | 76.82 | 27.9 | 0 | 6.07 | 5.6 | 4.4 | 12.48 | 3.46 | 607.61 |
| BOS3155 | Orsetti | 83.14 | 4.21 | 1.9 | 6.75 | 5.22 | 4.4 | 15 | 4.12 | 386.5 |
| H8892 | Heinz | 64.6 | 0.97 | 0.39 | 5.71 | 5.24 | 4.5 | 13.45 | 3.38 | 632.82 |
| LaRossa | Syngenta | 78.33 | 14.42 | 0.41 | 6.2 | 5.12 | 4.5 | 13.83 | 3.38 | 408.15 |
| Rpt1570 |  | 87.29 | 4.04 | 0 | 6.72 | 4.77 | 4.6 | 15.63 | 3.74 | 431.07 |

FURTHER EMBODIMENTS OF THE INVENTION

This invention also is directed to methods for producing a tomato plant by crossing a first parent tomato plant with a second parent tomato plant wherein either the first or second parent tomato plant contains the PSAF allele of the present invention. Further, this invention also is directed to methods for producing an inbred tomato line PSAF-derived tomato plant by crossing an inbred tomato line containing the allele PSAF with a second tomato plant and growing the progeny seed, and repeating the crossing and growing steps with the inbred tomato line PSAF-derived plant from 0 to 7 times. Thus, any such methods using a tomato line containing the PSAF allele are part of this invention: selfing, backcrosses, hybrid production, crosses to populations, and the like. All plants produced using a tomato line containing the PSAF allele as a parent are within the scope of this invention, including plants derived from inbred tomato lines having PSAF.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which tomato plants can be regenerated, plant calli, plant clumps and plant cells that are intact in plants or parts of plants, such as embryos, pollen, ovules, flowers, leaves, stalks, and the like.

As it is well known in the art, tissue culture of tomato can be used for the in vitro regeneration of tomato plants. Tissues cultures of various tissues of tomato and regeneration of plants therefrom are well known and published. By way of example, a tissue culture comprising organs has been used to produce regenerated plants as described in Girish-Chandel et al., *Advances in Plant Sciences.* 2000, 13: 1, 11–17, Costa et al., *Plant Cell Report.* 2000, 19: 3 327–332, Plastira et al., *Acta Horticulturae.* 1997, 447, 231–234, Zagorska et al., *Plant Cell Report.* 1998, 17: 12 968–973, Asahura et al., *Breeding Science,* 1995, 45: 455–459, Chen et al., *Breeding Science,* 1994, 44: 3, 257–262, Patil et al., *Plant and Tissue and Organ Culture.* 1994, 36: 2, 255–258. It is clear from the literature that the state of the art is such that these methods of obtaining plants are, and were, "conventional" in the sense that they are routinely used and have a very high rate of success. Thus, another aspect of this invention is to provide cells which upon growth and differentiation produce tomato plants having the physiological and morphological characteristics of a tomato line containing the PSAF allele.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed plants having the mutant allele.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed tomato plants, using transformation methods as described below to incorporate transgenes into the genetic material of the tomato plant(s).

Expression Vectors for Tomato Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase ll (nptll) gene, isolated from transposon Tn5, which when placed under the control of plant regulatory signals confers resistance to kanamycin. Fraley et al., *Proc. Natl. Aced. Sci. U.S.A.,* 80:4803 (1983) Eck et al., *Plant Cell Report,* 14:5 299–304 (1995). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.,* 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Charng et al., *Plant Science Limerick.* 1994, 98: 2, 175–183, Hu Wei e al., In vitro *Cellular and Developmental Biology Plant* 37:1 12–18 (2001), Agharbaoui et al., *Plant Cell Report* 15:1/2 102–105 (1995).

Recently, in vivo methods for visualizing GUS activity that do not require destruction of plant tissue have been made available. Molecular Probes publication 2908, Imagene Green__, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoters" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in tomato. Optionally, the inducible promoter is operably linked to a nucleotide sequence encoding a signal sequence which is operably linked to a gene for expression in tomato. With an inducible promoter the rate of transcription increases in response to an inducing agent.

Any inducible promoter can be used in the instant invention. See Ward et al., Plant Mol. Biol. 22:361–366 (1993). Exemplary inducible promoters include, but are not limited to, that from the ACEI system which responds to copper (Meft et al., PNAS 90:4567–4571 (1993)); In2 gene from maize which responds to benzenesulfonamide herbicide safeners (Hershey et al., Mol. Gen Genetics 227:229–237 (1991) and Gatz et al., Mol. Gen. Genetics 243:32–38 (1994)) or Tet repressor from Tn10 (Gatz et al., Mol. Gen. Genetics 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in tomato or the constitutive promoter is operably linked to a nucleotide sequence encoding a signal sequence which is operably linked to a gene for expression in tomato.

Many different constitutive promoters can be utilized in the instant invention. Exemplary constitutive promoters include, but are not limited to, the promoters from plant viruses such as the 35S promoter from CaMV (Odell et al., Nature 313:810–812 (1985), Tababeizadeh et al., Plant Cell Report 19:2 197–202 (1999), Kunik et al., Acta Horticulturae 447, 387–391 (1997) and the promoters from such genes as rice actin (McElroy et al., Plant Cell 2:163–171 (1990)); ubiquitin (Christensen et al., Plant Mol. Biol. 12:619–632 (1989) and Christensen et al., Plant Mol. Biol. 18:675–689 (1992)); pEMU (Last et al., Theor. Appl. Genet. 81:581–588 (1991)); MAS (Velten et al., EMBO J. 3:2723–2730 (1984)) and maize H3 histone (Lepetit et al., Mol. Gen. Genetics 231:276–285 (1992) and Atanassova et al., Plant Journal 2 (3): 291–300 (1992)).

The ALS promoter, Xba1/NcoI fragment 5' to the Brassica napus ALS3 structural gene (or a nucleotide sequence similarity to said Xba1/Ncol fragment), represents a particularly useful constitutive promoter. See PCT application WO96/30530.

C. Tissue-specific or Tissue-preferred Promoters

A tissue-specific promoter is operably linked to a gene for expression in tomato. Optionally, the tissue-specific promoter is operably linked to a nucleotide sequence encoding a signal sequence which is operably linked to a gene for expression in tomato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476–482 (1983) and Sengupta-Gopalan et al., Proc. Natl. Acad. Sci. U.S.A. 82:3320–3324 (1985)), such as the promoter rolD from Agrobacterium rhizogenes as mentioned in Grichko et al., Plant Physiology and Biochemistry 39:1 19–25 (2001); a leaf-specific and light-induced promoter such as that from cab or rubisco (Simpson et al., EMBO J. 4(11):2723–2729 (1985) and Timko et al., Nature 318:579–582 (1985)); an anther-specific promoter such as that from LAT52 (Twell et al., Mol. Gen. Genetics 217:240–245 (1989)); a pollen-specific promoter such as that from Zm13 (Guerrero et al., Mol. Gen. Genetics 244:161–168 (1993)) or a microspore-preferred promoter such as that from apg (Twell et al., Sex. Plant Reprod. 6:217–224 (1993). Signal Sequences for Targeting Proteins to Subcellular Compartments Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3–17 (1987), Lerner et al., Plant Physiol. 91:124–129 (1989), Fontes et al., Plant Cell 3:483–496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499–509 (1984), Steifel, et al., Expression of a maize cell wall hydroxyproline-rich glycoprotein gene in early leaf and root vascular differentiation, Plant Cell 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is tomato. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the Integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant mutant allele can be transformed with doned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae pv.* Tomato encodes a protein kinase); Mindrinos et al., *Cell* 78:1089 (1994) (Arabidopsis RSP2 gene for resistance to Pseudomonas syringae).

B. A Bacillus thuringiensis protein, a derivative thereof or a synthetic polypeptide modeled thereon. See, for example, Geiser et al., *Gene* 48:109 (1986), who disclose the cloning and nucleotide sequence of a Bt ä-endotoxin gene. Moreover, DNA molecules encoding ä-endotoxin genes can be purchased from American Type Culture Collection, Manassas, Va., for example, under ATCC Accession Nos. 40098, 67136, 31995 and 31998. See also Mandaokat et al., *Crop Protection.* 2000, 19:5, 307–312.

C. A lectin. See, for example, the disclose by Van Damme et al., *Plant Molec. Blol.* 24:25 (1994), who disclose the nucleotide sequences of several *Clivia miniata* mannose-binding lectin genes.

D. Genes coding for the coat proteins of the Cucumber Mosaic Comovirus (CMV), see Tomassoli et al., *Molecular Breeding.* 1999, 5: 2, 121–130, which once expressed in the plant allows it to be resistant to the CMV E. An enzyme inhibitor, for example, a protease or proteinase inhibitor or an amylase inhibitor or a polygalacturonase inhibitor protein. See, for example, Abe et al., *J. Biol.* *Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor l), Sumitani et al., *Biosci. Biotech. Biochem.* 57:1243 (1993) (nucleotide sequence of *Streptomyces nitrosporeus* a-amylase inhibitor). Powell et al., *Molecular Plant Microbe Interaction.* 2000, 13: 9 942–950 (tomatoes transformed with pear fruit polygalacturonase inhibitor protein to inhibit the fungal pathogen endopolygalacturonase).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-â, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo á-1, 4-D-polygalacturonases facilitate fungal colonization and plant nutrient release by solubilizing plant cell wall homo-á-1,4-D-galacturonase. See Lamb et al., Bio/Technology 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

S. A combination of Tobacco class 1 Chitinase and class 1 beta 1, 3, Glucanase gene that result in increased fungal resistance of the tomato expressing such genes. See Jongedijk et al., *Euphytica.* 1995, 85: 1/3, 173–180.

2. Genes That Confer Resistance to a Herbicide, For Example

A.. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. AppL. Genet.* 80:449 (1990), respectively.

B. Glyphosate (resistance impaired by mutant 5enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cydoshexones (ACCase inhibitor-encoding genes). See, for example, U. S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as

A. Increased flooding tolerance, for example by transforming a plant with a bacterial enzyme ACC deaminase. See Grichko et al., *Plant Physiology* and Biochemistry. 2001.39: 1, 19–25

B. Improved juice and pulp viscosity, by transforming the plant with an antisens gene of polygalacturonase. For example, see Porretta et al., Food *Chemistry.* 1998, 62: 3, 283–290, or Errington et al., *Journal of the Science of Food and Agriculture,* 1998. 76: 4, 515–519.

C. Reduced polyethylene production in order to better control the ripening of the fruit, by transforming the plant with a S-adenosylmethionine hydrolase. See Good et al., *Plant Molecular Biology.* 1994, 26: 3, 781–790.

D. Obtained male sterile plants, especially useful in hybrid tomato production, by introduction of a gene encoding a tobacco PR Glucanase as described in WO9738116.

Methods for tomato Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology,* Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Frary et al., *Plant Cell Report.* 1996, 16: 3/4, 235–240, Roehel et al., *Plant Cell Report.* 1993,12: 11, 644–647, Hu-Wei et al., In *Vitro Cellular and Developmental Biology Plant.* 2001 37: 1, 12–18. *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev.*

*Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 6.198.022 issued Mar. 6, 2001.

B. Direct Gene Transfer

Despite the fact the host range for Agrobacterium-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 lm. The expression vector Is introduced Into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992), Baum et al., *Plant Journal.* 1997, 12: 2, 463–469, Eck et al., *Plant Cell Report.* 1995, 14: 5, 299–304, Manzara et al., *Plant Molecular Biology Reporter* 12 :3 221–226 (1994).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.,* 4:2731 (1985), Christou et al., *Proc Natl. Acad. Sci.* U.S.A. 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of Vllth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994) A transfer of chromosome has been reported from a transformed donor line of potato to a recipient line of tomato through microprotoplast PEG induced fusion. See Ramalu et al., *Theorical and Applied Genetics* 92:: 316–325 (1996).

Following transformation of tomato target tissues, expression of the above-described selectable marker genes allows for preferential selection of transformed cells, tissues and/or plants, using regeneration and selection methods now well known in the art.

The foregoing methods for transformation would typically be used for producing a transgenic plant. The transgenic plant could then be crossed, with another (non-transformed or transformed) plant, in order to produce a new transgenic plant. Alternatively, a genetic trait which has been engineered into a particular tomato line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a line which does not contain that gene. As used herein, "crossing" can refer to a simple X by Y cross, or the process of backcrossing, depending on the context.

When the term inbred tomato plant is used in the context of the present invention, this also includes any single gene conversions of that inbred. The term single gene converted plant as used herein refers to those tomato plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental tomato plants for that inbred. The parental tomato plant which contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility such as the PR glucanase gene, herbicide resistance such as pat or bar genes, resistance for bacterial, fungal (such as I genes used for resistance to fusarium oxysporum), or viral disease (such as genes TM1 and TM2 used for TMV resistance), insect resistance such as Cry1Ac orMi genes, male fertility, enhanced nutritional quality, enhanced sugar content, enhanced processing qualities as shown in U.S. Pat. 6,072, 106 by increasing the content in soluble solids, enhanced conservation and delayed ripening such as in using nor or rin genes, yield stability and yield enhancement. These genes are generally inherited through the nucleus. Some other known male sterility genes are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

DEPOSIT INFORMATION

Tomato seed containing the PSAF mutant allele have been placed on deposit with the American type Culture Collection (ATCC), 10801 University Boulevard, Manassas, Va. 20110-2209 on Dec. 12, 2002 and having Deposit Accession Number PTA-4857.

Although the foregoing invention has been described in some detail by way of illustration and example for purposes of clarity and understanding. However, it will be obvious that certain changes and modifications such as single gene modifications and somaclonal variants, variant individuals selected from large populations of the plants and the like may be practiced within the scope of the invention, as limited only by the scope of the appended claims.

What is claimed is:

1. A tomato seed containing an allele for the allflesh trait designated PSAF, wherein said allele is present in seed deposited under ATCC Accession No. PTA-4857.

2. A tomato plant produced by growing the seed of claim 1.

3. Pollen of the plant of claim 2.

4. An ovule of the plant of claim 2.

5. A tissue culture comprising regenerable cells of the plant of claim 2, wherein said cells of the tissue culture are produced from a plant part selected from the group consisting of leaves, pollen, embryos, cotyledons, hypocotyls, meristematic cells, roots, root tips, pistils, anthers, flowers, and stems, and wherein said cells contain a PSAF allele.

6. A tomato plant regenerated from said tissue culture of claim 5, wherein said plant contains a PSAF allele, and wherein seed containing said PSAF allele was deposited under ATCC Accession No. PTA-4857.

7. A method for producing F1 hybrid tomato seed comprising crossing a first parent tomato plant with a second parent tomato plant and harvesting the resultant F1 hybrid tomato seed, wherein said first or second parent tomato plant is the tomato plant of claim 2.

8. A first generation (F1) hybrid tomato plant produced by growing said hybrid tomato seed of claim 7, wherein said hybrid contains the PSAF allele.

9. A tomato plant, or a part thereof, produced by growing the seed resulting from the plant of claim 8, wherein said seed and said plant contain the PSAF allele.

10. Tomato seeds or plants, each derived from seeds deposited under ATCC Accession No. PTA-4857 wherein said seeds and plants contain the allele designated PSAF.

11. The seed of claim 1 wherein said allele is recessive.

12. The seed of claim 10 wherein said seed is a hybrid seed.

13. The seed of claim 10 wherein said seed in an inbred seed.

* * * * *